(12) United States Patent
McNair

(10) Patent No.: US 9,633,171 B2
(45) Date of Patent: Apr. 25, 2017

(54) PREDICTING NEONATAL HYPERBILIRUBINEMIA

(71) Applicant: CERNER INNOVATION, INC., Kansas City, KS (US)

(72) Inventor: Douglas S. McNair, Leawood, KS (US)

(73) Assignee: CERNER INNOVATION, INC., Kansas City, KS (US)

( * ) Notice: Subject to any disclaimer, the term of this patent is extended or adjusted under 35 U.S.C. 154(b) by 667 days.

(21) Appl. No.: 14/139,573

(22) Filed: Dec. 23, 2013

(65) Prior Publication Data

US 2014/0114583 A1 Apr. 24, 2014

Related U.S. Application Data

(62) Division of application No. 12/645,736, filed on Dec. 23, 2009, now Pat. No. 9,495,514.

(60) Provisional application No. 61/142,265, filed on Jan. 2, 2009.

(51) Int. Cl.
*G01N 33/48* (2006.01)
*G06F 19/00* (2011.01)

(52) U.S. Cl.
CPC ........ *G06F 19/345* (2013.01); *G06F 19/3437* (2013.01); *G06F 19/363* (2013.01)

(58) Field of Classification Search
CPC .................................................... G06F 19/345
USPC ......................................................... 702/19
See application file for complete search history.

(56) References Cited

U.S. PATENT DOCUMENTS 5,804,405 A 9/1998 Ahlfors
2010/0062948 A1 3/2010 Kleinfeld et al.

OTHER PUBLICATIONS

Non-Final Office Action dated Nov. 26, 2014 in U.S. Appl. No. 12/645,736, 5 pages.
Final Office Action dated Jul. 30, 2015 in U.S. Appl. No. 12/645,736, 8 pages.
Notice of Allowance dated Sep. 8, 2016 in U.S. Appl. No. 12/645,736, 7 pages.
Non-Final Office Action dated May 18, 2016 in U.S. Appl. No. 12/645,736, 11 pages.
Berk, P., et al., Studies of bilirubin kinetics in normal adults., J Clin Invest., 1969;48:2176-90.
Bhutani, V., et al., Predictive ability of a pre-discharge hour-specific serum bilirubin for subsequent significant hyperbilirubinenmia in healthy term and near-term newborns, Pediatrics 1999; 103:6-14.
Boo, N., et al., Prediction of severe hyperbilirubinaemia using the Bilicheck transcutaneous bilirubinometer. J Paediatr Child Health., 2007;43:297-302.
Dennery, P., et al., Neonatal blue-light phototherapy could increase the risk of dysplastic nevus development. Pediatrics. 2007;120:247-8.
Dennery, P., et al., Neonatal Hyperbilirubinemia., New England Journal of Medicine 2001; 334:581-90.
Dennery, P., Pharmacological interventions for the treatment of neonatal jaundice. Semin Neonatol. 2002;7:111-9.
Facchini, F., et al., Follow-up of neonatal jaundice in term and late premature newborn. J Pediatr (Rio J) 2004; 83:313-22.
Gartner, L., et al., Jaundice and breastfeeding Pediatr Clin North Am 2001; 48:389-99.
Gloria-Bottini, F., et al., Adenosine deaminase genetic polymorphism and the effect of smoking on neonatal bilirubinemia and developmental parameters. Early Hum Dev. Jun. 16, 2008.
Jangaard, K., et al., Outcomes in a population of healthy term and near-term infants with serum bilirubin levels >=19 mg/dL who were born in Nova Scotia, Canada, between 1994 and 2000. Pediatrics. 2008;122:119-24.
Kaplan, M., et al., Evaluation of discharge management in the prediction of hyperbilirubinemia: the Jerusalem experience. J. Pediatr. 2007;150:412-7.
Keren, R., et al., A comparison of alternative risk-assessment strategies for predicting significant neonatal hyperbilirubinemia in term and near-term infants. Pediatrics. 2008;121:e170-9.
Kuzniewicz, M., et al., Risk factors for severe hyperbilirubinemia among infants with borderline bilirubin levels: a nested case-control study. J. Pediatr. 2005;153:234-40.
Moerschel, S., et al., A practical approach to neonatal jaundice. Am Fam Physician. 2008; 77:1255-62.
Ostrow, J., et al., Phototherapy for neonatal jaundice. N. Engl J Med. 2008;358(23):2534.
Zanardo. V., et al., Cytokines in human colostrum and neonatal jaundice. Pediatr Res. 2007;62:191-4.
Subcommittee on Hyperbilirubinemia, Management of Hyperbilirubinemia in the Newborn Infant 35 or More Weeks of Gestation, Pediatrics 2004; 114;297-316.
Gillespie, Robert S., et al., One size does not fit all: Interpreting Laboratory Data in Pediatric Patients, AMIA 2003 Symposium Proceedings—p. 850.
Setia, Sabeena, et al., Neonatal Jaundice in Asian, White and Mixed-Race Infants, Arch Pediatr Adolesc Med., vol. 156, Mar. 2002.
Bjerre, J, et al., Surveillance of extreme hyperbilirubinaemia in Denmark: A method to identify the newborn infants. Acta Paediatr. 2008;97:1030-4.

(Continued)

*Primary Examiner* — Jerry Lin
(74) *Attorney, Agent, or Firm* — Shook, Hardy & Bacon L.L.P.

(57) ABSTRACT

A multi-variable statistical predictive leading-indicator approach is employed for identifying newborns at risk of clinically significant hyperbilirubinemia and for determining to administer interventions to at-risk newborns. In embodiments, a multi-variable logistic regression statistical model capable of calculating a probability of clinically significant hyperbilirubinemia is generated. Using an input data set for a newborn and the multi-variable logistic regression statistical model, a probability of clinically significant hyperbilirubinemia is determined for the newborn and presented to a clinician.

9 Claims, 6 Drawing Sheets

(56) References Cited

OTHER PUBLICATIONS

Petrone, E, et al., Early hospital discharge of the healthy term neonate: the Italian perspective. Minerva Pediatr. 2008;60:273-6.
Shortland, D., et al., Understanding neonatal jaundice; U.K. practice and international profile. J R Soc Health. 2008;128:202-6.
Ivanciuc, O., Applications of Support Vector Machines in Chemistry, Reviews in Computational Chemistry, vol. 23., 2007, p. 291.
Huang et al. "Risk Factors for Sever Hyperbilirubinemia in Neonates", Pediatric Research (2004) vol. 56, No. 5, pp. 682-689.

FIG. 5

PREDICTING NEONATAL HYPERBILIRUBINEMIA

CROSS-REFERENCE TO RELATED APPLICATIONS

This application is a divisional of, and claims priority from, U.S. patent application Ser. No. 12/645,736, entitled "PREDICTING NEONATAL HYPERBILIRUBINEMIA," filed Dec. 23, 2009, which claims the benefit of U.S. Provisional Application No. 61/142,265, entitled "METHOD AND SYSTEM FOR PREDICTING NEONATAL HYPERBILIRUBINEMIA," filed Jan. 2, 2009, both of which are incorporated by reference herein in their entirety.

BACKGROUND

Neonatal hyperbilirubinemia, defined as a total serum bilirubin level above 5 mg/dL (86 micromolar), is a frequently encountered clinical problem. Although up to sixty percent of term newborns have clinical jaundice in the first week of life, few have significant underlying disease. High bilirubin levels that are prolonged may lead to a variety of central nervous system abnormalities, developmental delays, retardation, and other serious health impairments and even death.

Clinical jaundice typically results from the presence of high concentrations of unconjugated bilirubin pigment in the skin and mucus membranes. FIG. 2 shows the biochemical pathways for metabolizing and excreting bilirubin, as known to those of skill in the art. Depending on the underlying etiology, this condition can present throughout the neonatal period. Bilirubin is the final product of heme degradation. At physiologic pH, bilirubin is insoluble in plasma and requires protein binding with albumin. After conjugation in the liver, it is excreted in bile. Newborns produce bilirubin at a rate of approximately 6 to 8 mg per kg per day. This is more than twice the production rate in adults, primarily because of relative polycythemia and increased red blood cell turnover in neonates. The rate of bilirubin production in mg/kg/24 h typically declines to the adult rate of 3.8±0.6 mg/kg/24 h within 10 to 14 days after birth.

Although glucuronidation is one of the most important routes of biotransformation, the broad and overlapping substrate specificity of the hepatic uridine diphosphate glucuronosyltransferases UDP-glucuronosyltransferases (UGTs) that catalyze glucuronidation remains poorly understood. The two main reasons for this situation are the lack of isolated individual UGT isozymes and the lack of assay methods suitable for detecting glucuronidation of diverse compounds. The UDP-glucuronosyltransferases are a family of enzymes that catalyze the glucuronidation of endogenous compounds (such as bilirubin) and xenobiotic compounds (such as drugs), generating products that are more hydrophilic and thus more readily excreted in bile or urine. UGTs are 50-60 kDa integral membrane proteins with the major portion of the protein, including the catalytic domain, located in the lumen of the endoplasmic reticulum and a C-terminal anchoring region spanning the ER membrane. Two UGT families—UGT1 and UGT2—have been identified in humans. Although the members of these families are less than 50% identical in primary amino acid sequence, they exhibit significant overlap in substrate specificity.

The members of the UGT1 family that are expressed in human liver, where the majority of xenobiotic metabolism takes place, include UGT 1A1, 1A3, 1A4, 1A6, and 1A9. Although the UGT2 family has not been studied as extensively, it is known that UGT 2B4, 2B7, 2B10, 2B15 and 2B17 are expressed in the liver. Mutations in UGTs are known to have deleterious effects, including clinical hyperbilirubinemia.

Organic-anion transporter proteins (OATP) are cell membrane proteins that accomplish the transfer of organic compounds into and out of the liver cells so that UGT and other enzymes can metabolize the compounds. OATPs are, like UGTs, developmentally sensitive to gestational age and other factors. OATP 1B1, 1B3, and 2B1 have been studied most to-date. Both OATPs and UGTs are involved in the metabolism and excretion of bilirubin.

Infant jaundice, or hyperbilirubinemia, is a significant clinical problem, occurring in about sixty percent of full-term and near-term infants. The syndrome is the direct result of increased bilirubin levels in the infant body. The organic-anion transport and glucuronidation metabolic pathways are not fully developed in neonates, particularly in premature neonates. Nevertheless, some near-term or term neonates, are subject to perinatal jaundice as well. Often, such infants are dismissed from hospital with moderate bilirubin levels, only to return requiring readmission to hospital several days later with markedly increased bilirubin and jaundice. High bilirubin levels that are prolonged may lead to a variety of central nervous system abnormalities, developmental delays, retardation, and other serious health impairments and even death. Apart from the morbidity associated with neonatal hyperbilirubinemia, there is significant financial loss and waste of health services resources connected with the hyperbilirubinemic readmissions to hospital.

Bilirubin is a bile pigment which is a metabolic product of heme formed from the degradation of hemoglobin in erythrocytes by reticuloendothelial cells. It can also be formed by the breakdown of other heme-containing proteins such as cytochromes. The most typical biological form of bilirubin is bilirubin IXa.

Bilirubin IXa normally circulates in the plasma of the bloodstream in several forms. One form has been designated as "unconjugated" or "indirect" bilirubin. The unconjugated bilirubin may complex to serum albumin and, as such, is designated as "bound" unconjugated bilirubin, or it may exist in a non-albumin bound or free form and, as such, is designated as "unbound" unconjugated bilirubin. Both bound and unbound unconjugated bilirubin are normally transported to the liver, wherein they are taken up by the liver cells and converted to a polar conjugate form. The conversion typically involves the transfer of glucuronic acid molecules, catalyzed by the enzyme hepatic glucuronyl transferase, to the unconjugated bilirubin. This converted bilirubin is designated in the art as "conjugated" or "direct" bilirubin. Some of the conjugated bilirubin may leak back into the bloodstream. Conjugated bilirubin in the bloodstream, like unconjugated bilirubin, can bind to albumin, although the unconjugated form seems to bind to albumin more tightly. Thus, bilirubin in the blood exists in four forms: (1) bound conjugated bilirubin, (2) unbound conjugated bilirubin, (3) bound unconjugated bilirubin and (4) unbound unconjugated bilirubin. To summarize, (1) and (2) together are known as "direct" bilirubin, while (3) and (4) together are termed "indirect" bilirubin. These four fractions generally comprise the serum or plasma bilirubin concentration. However, a fifth component, delta bilirubin, has been described which is a bilirubin covalently linked to albumin. It is typically a very small fraction of the total bilirubin.

Unconjugated but not conjugated bilirubin can poison many vital cell functions, and a variety of experimental and clinical evidence suggests that unbound unconjugated bilirubin is a potential neurotoxin. Specifically, since it is not restricted by albumin binding, unbound unconjugated bilirubin can act as a neurotoxin because of its ability to migrate from the vascular space into the nervous system where it can complex with nervous tissue causing irreversible damage. Typically, unbound unconjugated bilirubin comprises less than 0.05% of the fraction of total bilirubin in the blood and is therefore difficult to measure. Disease states resulting in elevated levels of serum bilirubin may raise either "conjugated" or "unconjugated" levels of bilirubin or both forms simultaneously. However, only elevated unconjugated and unbound forms predispose a patient to neurological bilirubin toxicity.

Newborn infants suffering from high levels of unconjugated bilirubin (i.e., hyperbilirubinemia) become jaundiced after birth and are susceptible to developing kernicterus, which is an accumulation of unconjugated bilirubin in tissues of the nervous system, particularly the basal ganglia of the developing brain. This condition, also designated as bilirubin encephalopathy, may produce athetoid cerebral palsy, ocular palsy, deafness, mental retardation, and defects in fine motor control and cognitive function. Neonates afflicted with hemolysis and infants born prematurely compose the highest risk groups for bilirubin encephalopathy; however, kernicterus has also been reported in jaundiced term newborns with no clear pathological etiology for their jaundice.

Most newborns develop transient unconjugated hyperbilirubinemia in the first few days of life. There has been a recent resurgence in bilirubin encephalopathy (kernicterus) in term and near term newborns that has been attributed both to early postnatal hospital discharge and less concern about bilirubin toxicity by health care providers.

Various treatments have been suggested for both infant jaundice when these problems occur. These treatments include phototherapy and, in some cases, exchange transfusions, extracorporeal filtration systems, and drugs which induce a more efficient clearance of bilirubin from the body. None of these treatments is simple to administer. None is effective without negative side reactions, including risk of injury or death. If the jaundice is not promptly treated, serious damage to the nervous system can result, especially in infants, as the elevated amounts of bilirubin act as a neurotoxin, and the blood/brain barrier in infants is incompletely developed. Also, the foregoing treatments are administered after the fact—i.e., after the jaundice has already appeared and typically after the jaundice has become severe and prolonged.

In neonates, the visible signs of the disorder manifest themselves usually at 72 hours or later after birth, generally after the infant has left the hospital or birth center. Thus, the signs of hyperbilirubinemia typically appear when the baby is no longer under the observation of trained medical personnel. This delayed onset of neonatal hyperbilirubinemia is also at a time when many mothers have strong psychological tendencies to hope and believe that their newborn is well. This perceptual and psychological bias often leads to significant delays in the mothers' seeking care from pediatric physicians and nurses. In order to minimize the organic and neurological damage caused by the elevated bilirubin levels, therefore, it is advantageous to intervene early, preferably prior to the baby's discharge from the hospital or birthing center and before medical control over monitoring and treatment has been lost, which is often before the visible signs of jaundice appear.

One aspect of effective intervention is the accurate and timely identification of individuals at risk for developing this syndrome. Because, in order to eliminate as totally as possible the incidence of neonatal jaundice, every infant must be tested, effective prediction requires a simple, non-invasive procedure. Measurement of bilirubin in the blood per se is not a satisfactory approach because accurate prediction of a potential to develop jaundice rests on detection of increased bilirubin production, as opposed to the levels of bilirubin in the blood. Blood bilirubin levels are influenced not only by production, of course, but also by rates of excretion, and hepatic and intestinal uptake. When subjects at risk are identified, they must either be monitored for subsequent treatment or administered a treatment in advance which prevents the onset of serious jaundice.

Prior art approaches to identification of individuals at risk for developing neonatal hyperbilirubinemia have several limitations. When only one variable is measured (such as total bilirubin, as used in the Bhutani nomogram and similar decision tools), the sensitivity and specificity are not adequate to accurately define the individual infants in the population at-risk. When one variable (such as total bilirubin) is measured serially, the invasiveness and exposure of the infant to repeated phlebotomies is usually unacceptable, to the clinicians and to the parents. When more than one variable is measured, the predictive decision-support method generally is intolerant of missing values for one or more variables and fails to recommend a decision or produce a risk-score when some information is not available. When exotic laboratory variables (such as OATP or UGT genotypes, or TNF-alpha or IL-1$\beta$, IL-6, IL-8, IL-10, or other biomarkers) are measured, one or more of the following attributes of the assay methods preclude their widespread practical implementation: excessive turnaround-time in the context of relatively short time interval that is pertinent to the clinical decision regarding what preventive or management interventions, if any, are applicable; excessive testing expense; lack of ready availability of providers of the assay methods.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention provide a multi-variable statistical predictive leading-indicator system and method for a prevention regime with a screening procedure to provide a systematic program for prevention of neonatal jaundice. The approach can be applied in connection with policies and procedures for administering phototherapy prophylactically, holding the baby in the hospital nursery for additional time beyond that which would be ordinarily associated with the delivery episode, or other interventions to prevent and manage incipient neonatal hyperbilirubinemia.

In embodiments, the screening procedure involves the use of a single timed blood specimen and simple chemistry and hematology tests that are routinely available in hospital laboratories. A multivariable statistical predictive score is calculated from the results of such tests. Subjects found to be at elevated risk in this simple screening procedure then receive interventions designed to prevent the onset of this syndrome or to manage the severity of the syndrome if it has already developed. The use of the screen avoids the disruption and expense and side-effects that would be entailed by applying the interventions to all infants. The score-guided selective use of the interventions permits the entire at-risk subpopulation to be protected while simultaneously preventing adverse effects associated with phototherapy or other interventions.

Thus, in one aspect, embodiments are directed to a method to prevent the occurrence of neonatal jaundice in a population of human infants which comprises, first, screening the members of the population for above-normal risk of neonatal hyperbilirubinemia, and, second, administering to members of this population who exhibit above-normal risk, appropriate interventions effective to reduce the production of bilirubin or to facilitate the metabolism and excretion of the bilirubin that is produced. In another aspect, the invention is directed to software systems embodiments effective in practicing this method.

One embodiment of the present invention is directed to a method to prevent the occurrence of neonatal jaundice in a population of human infants. The method includes administering selected interventions to a set of members of the population who exhibit above-threshold values of a multi-variable predictive score calculated at least in part from laboratory test results measured at a known time following birth.

In another aspect of the invention, an embodiment is directed to one or more computer storage media storing computer-useable instructions that, when used by one or more computing devices, cause the one or more computing devices to perform a method. The method includes generating a multi-variable logistic regression statistical model capable of calculating a probability of clinically significant hyperbilirubinemia. The method also includes receiving an input data set for a human infant based on laboratory test results for the human infant and determining a probability of clinically significant hyperbilirubinemia for the human infant based on the input data set and the multi-variable logistic regression statistical model. The method further includes communicating for presentation to a clinician the probability of clinically significant hyperbilirubinemia for the human infant.

A further embodiment of the present invention is directed to one or more computer storage media storing computer-useable instructions that, when used by one or more computing devices, cause the one or more computing devices to perform a method. The method includes: (a) receiving training data associated with a plurality of human infant cases, the plurality of human infant cases having been selected based on inclusion-exclusion criteria, the training data including data for a plurality of variables; (b) partitioning the training data into a training data subset and a test data subset, each of the training data subset and the test data subset including training data associated with a portion of the plurality of human infant cases; (c) employing a machine-learning technique to generate a classifier based on the training data subset; (d) assessing whether the classifier satisfies a predetermined receiver operating characteristic (ROC) c-statistic; (e) if the classifier does not satisfy the predetermined ROC c-statistic, repeating (c) and (d) until a classifier is generated that satisfies the predetermined ROC c-statistic; (f) if the classifier satisfies the predetermined ROC c-statistic, validation testing the classifier using the test data subset; (g) assessing whether an optimum minimum has been achieved based on output from the validation testing; (h) if an optimum minimum has not been achieved, repeating (c)-(g) until an optimum minimum has been achieved; (i) if an optimum minimum has been achieved, generating a logistic regression model; (j) assessing whether statistical performance of the logistic regression model satisfies a predetermined requirement; (k) if the statistical performance of the logistic regression model does not satisfy the predetermined requirement, repeating (c)-(j) until a logistic regression model is generated that satisfies the predetermine requirement; (l) receiving input data for a human infant; (m) calculating a probability of clinically significant hyperbilirubinemia using the input data for the human infant and the logistic regression model; (n) comparing the calculated probability to one or more thresholds for hyperbilirubinemia intervention to determine one or more risk levels; and (o) communicating for presentation to a clinician the one or more risk levels.

As can be appreciated, significant savings can be realized through systematic methodology to prospectively identify those infants who are at high risk of becoming severely hyperbilirubinemic and undertake preventive and management interventions to mitigate the risk, including prophylactic or preemptive phototherapy and holding such infants in-hospital for one to several days longer than would otherwise be done.

BRIEF DESCRIPTION OF THE DRAWINGS

The present invention is described in detail below with reference to the attached drawing figures, wherein:

FIG. 5 is an illustrative screen display of an exemplary view for an online form which receives and retrieves the necessary variables' values and calculates the logistic regression hyperbilirubinemia risk score in accordance with an embodiment of the present invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Figure 1:
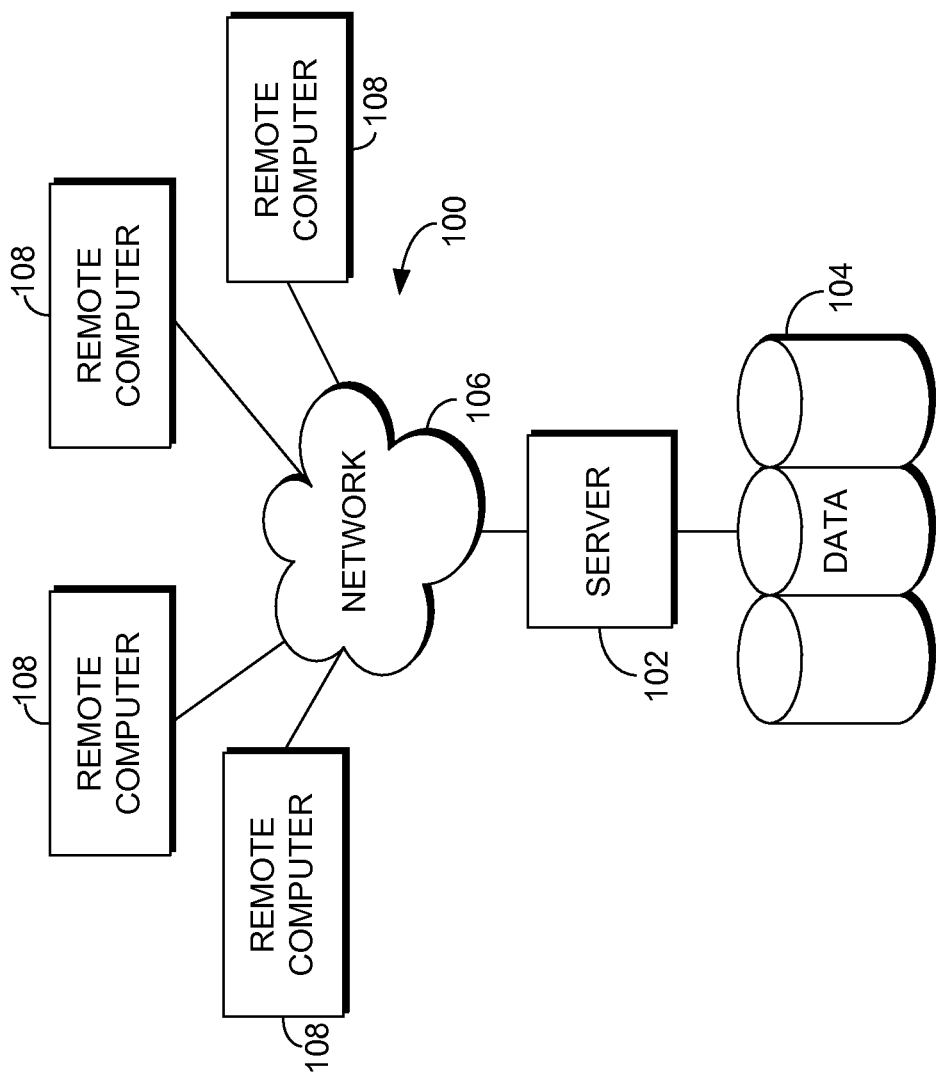
FIG. 1 is a block diagram of an exemplary computing environment suitable for use in implementing the present invention.
Figure 2:
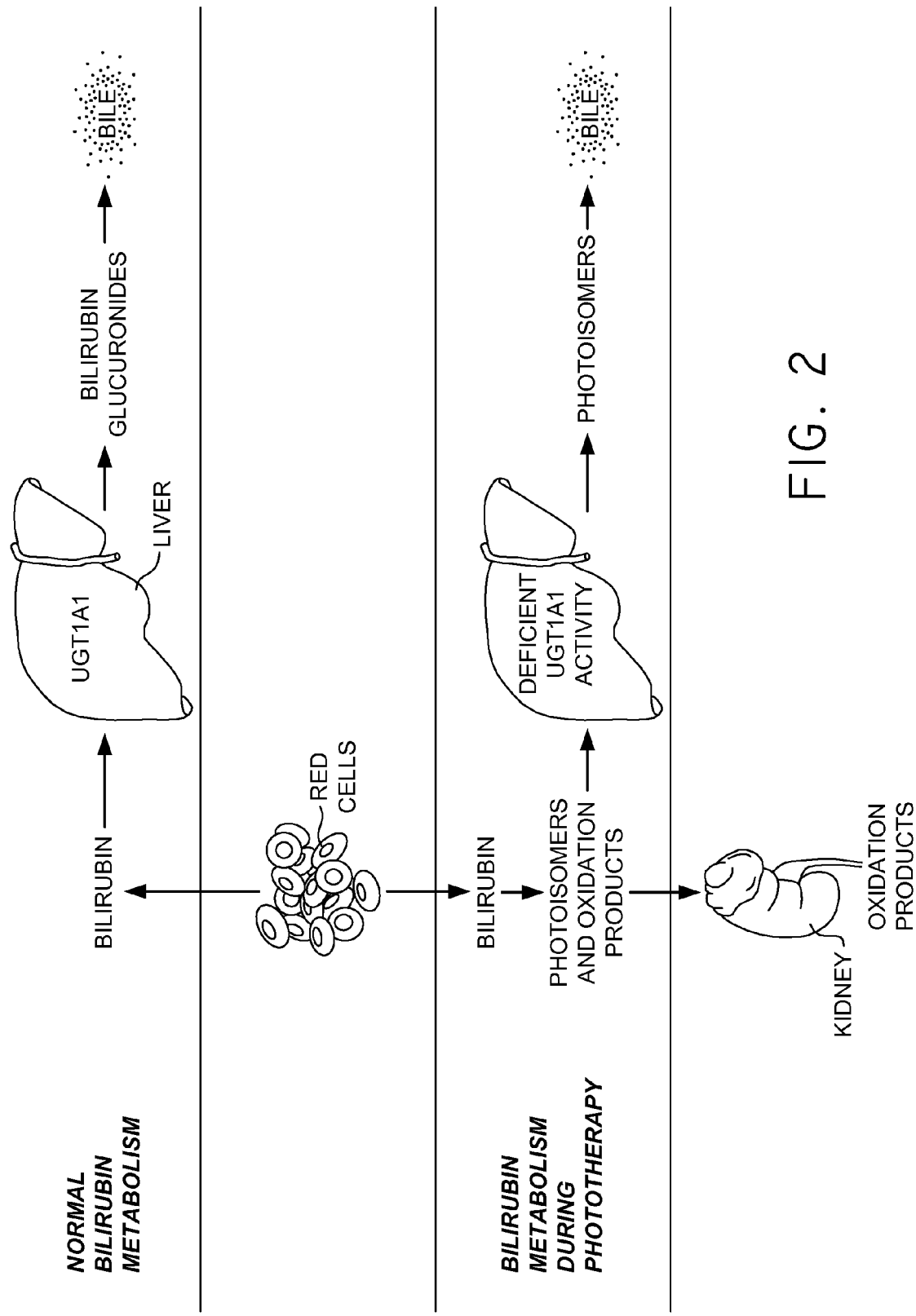
FIG. 2 shows the biochemical pathways for metabolizing and excreting bilirubin, as known to those of skill in the art.

Referring to the drawings in general, and initially to FIG. 1 in particular, an exemplary computing system environment, for instance, a medical information computing system, on which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a server 22. Components of the server 22 may include, without limitation, a processing unit, internal system memory, and a suitable system bus for coupling various system components, including database cluster 24, with the server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 22 typically includes, or has access to, a variety of computer readable media, for instance, database cluster 24. Computer readable media can be any available media that may be accessed by server 22, and includes volatile and nonvolatile media, as well as removable and non-removable media. By way of example, and not limitation, computer readable media may include computer storage media and communication media. Computer storage media may include, without limitation, volatile and non-volatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for the server 22.

The server 22 may operate in a computer network 26 using logical connections to one or more remote computers 28. Remote computers 28 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the components described above in relation to the server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the server 22 may include a modem or other means for establishing communications over the WAN, such as the Internet. In a networked environment, program modules or portions thereof may be stored in the server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., server 22 and remote computers 28) may be utilized.

In operation, a user may enter commands and information into the server 22 or convey the commands and information to the server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 22. In addition to a monitor, the server 22 and/or remote computers 28 may include other peripheral output devices, such as speakers and a printer.

Although many other internal components of the server 22 and the remote computers 28 are not shown, those of ordinary skill in the art will appreciate that such components and their interconnection are well known. Accordingly, additional details concerning the internal construction of the server 22 and the remote computers 28 are not further disclosed herein.

Figure 3A:
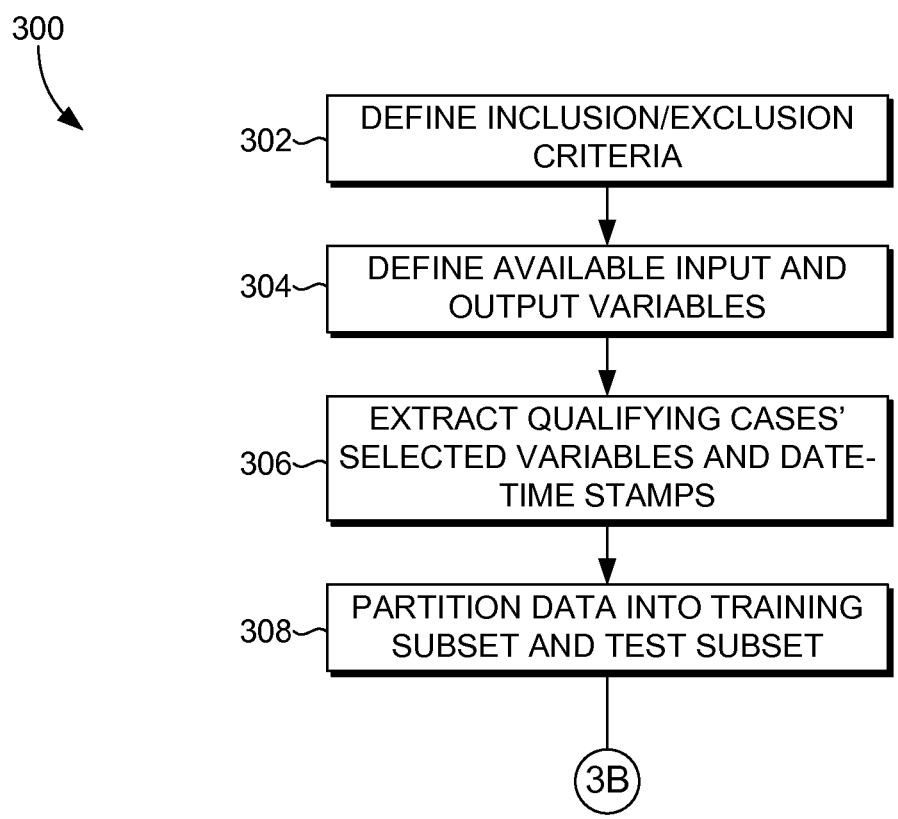
FIGS. 3A and 3B include a flow diagram showing a method for producing and validating a statistical model for accurately predicting neonatal hyperbilirubinemia in accordance with an embodiment of the present invention.
Figure 3B:
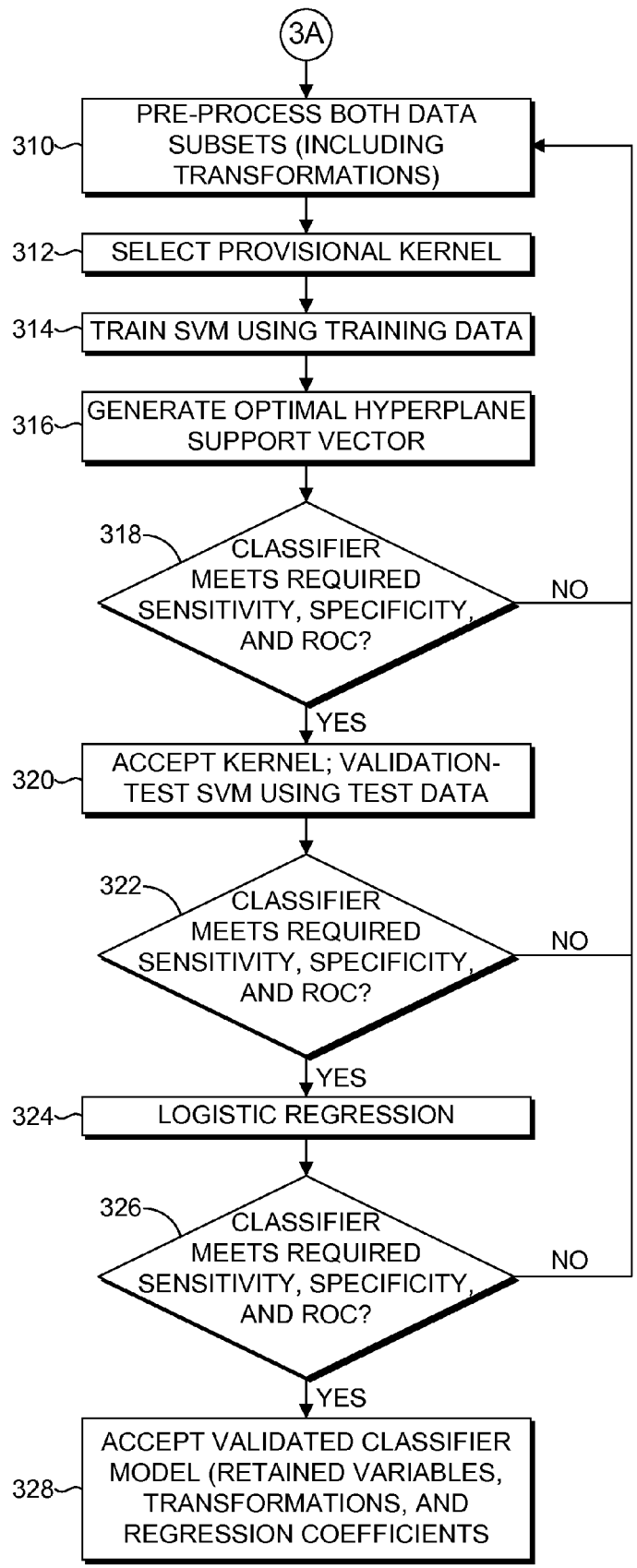

Turning to FIGS. 3A and 3B, a flow diagram is provided that illustrates a method 300 for producing and validating a statistical model for accurately predicting neonatal hyperbilirubinemia in accordance with an embodiment of the present invention. Initially, inclusion-exclusion criteria is defined, as shown at block, as well as problem specification in terms of available input and output variables, at block 304. Thereafter, as shown at block 306, training data is collected. Training data comprises a set of data points having known characteristics. This data may come from research facilities, academic institutions, commercial entities, and/or other public or confidential sources. In the case of the present exemplary embodiment, the data came from an anonymized datawarehouse of U.S. hospitals' electronic medical record data for newborns. The collection of training data may be accomplished manually or by way of an automated process, such as known electronic data transfer methods. Accordingly, an exemplary embodiment of the learning machine for use in conjunction with the present invention may be implemented in a networked computer environment.

With reference again to block 302, it is known to those practiced in the art that to construct an effective classifier, appropriate inclusion-exclusion criteria is first defined in sufficient detail that the cases acquired for the purpose of classifier design accurately represent the population to which the classifier is intended to be applied. By way of example only and not limitation, in an exemplary embodiment of the present invention, the inclusion criteria includes near-term neonates. The term "near-term neonates" is used herein to mean those with gestational ages between 35 weeks and 41 weeks inclusive. Birth weight less than 2,000 gm may be used in an embodiment as a surrogate variable for excluding cases regardless of recorded estimated gestational age. Meconium-stained amniotic fluid, early onset neonatal sepsis (septic shock), congenital malformations, and parental HIPAA informed decline to consent to allow data to be used for research may also be used as exclusion criteria. Some criteria for case inclusion in classifier development pertain to the dependent variables or 'outcomes' that are the object of the classification. In some embodiments of the present invention, the existence of at least one bilirubin determination prior to newborn discharge from hospital plus the existence of one or more care episodes within the first 30 days following newborn discharge is used as case inclusion criteria.

With reference again to block 304, for the cohort meeting the applicable inclusion-exclusion criteria, database retrieval of extant electronic medical records is performed. This serves to define the available input and output clinical and laboratory variables and characterize the descriptive statistics of each variable and assess the degree of "missingness" of information for each variable. In one embodiment, variables whose values are missing at a greater than 20% rate are excluded from subsequent consideration in classifier construction and development. It should be understood that although database retrieval of electronic medical records is described, any type of patient medical or health record may be utilized within the various embodiments of the present invention (in the context of method 300 or in other contexts of embodiments of the present invention).

Next, at block 306, information for the qualifying cases for each of the selected variables is extracted from the electronic medical record or other data source, including the date-time stamp for each item. As shown at block 308, the retrieved cases and case information are partitioned into two subsets—a first subset that is to be utilized for classifier construction and training (training data subset), and a second subset that is to be used for classifier validation testing (test data subset). Any of a variety of partitioning methods can be employed such as are well-known to statisticians practiced in the art. Randomized 'bootstrap' sampling without replacement, for example, may be used to insure that the subsets that are generated are not biased with regard to time, source institutions, or other factors. In some embodiments, the partitioning is made into two subsets of equal size (50%-50%). However, there is no requirement that this be the case. The subsets can be of different sizes. In some embodiments, the sample size of each subset is sufficient to achieve a desired 80% or greater statistical power for classification of the cases.

As shown at block 310, statistical pre-processing is performed, including calculation of mean, median, standard deviation, skewness, and kurtosis for each of the numerical variables and frequency tables for each of the categorical variables. In instances where the statistical distribution of a numerical variable is markedly skewed, then logarithmic or power-law or other transformation of that variable is performed by methods that are well-known to statisticians, so as to produce a distribution for the transformed variable that is symmetrical and more nearly Gaussian in shape than that of the raw variable. The collected training data is optionally pre-processed in order to allow the learning machine to be applied most advantageously toward extraction of the knowledge inherent in the training data. During this preprocessing stage, a variety of different transformations can be performed on the data to enhance its usefulness. Such transformations, examples of which include addition of expert information, spline conversion, logarithmic or power-law transformations, etc., will be readily apparent to those of skill in the art. However, the preprocessing of interest in an embodiment of the present invention is the reduction of dimensionality by way of feature selection.

The resulting dataset is processed with a Support Vector Machine (SVM) algorithm and a provisional kernel is selected, as shown at block 312. A SVM is a specific type of learning machine that implements a specialized algorithm for providing generalization when estimating a multi-dimensional function from a limited collection of data. The training data subset is used to condition the SVM kernel coefficients and generate a support vector (or hyperplane of the variables) at block 316 that optimally distinguishes the cases according to the dependent variable, which in one embodiment of the present invention is the outcome of re-admission to hospital for hyperbilirubinemia less than 10 days following newborn discharge. A SVM may be used in estimating classification functions (e.g., pattern-recognition problems) and real-valued functions (e.g., function approximation problems and regression estimation problems). Those skilled in the art should appreciate that SVMs are capable of processing input data having extremely large dimensionality. However, in some embodiments, pre-processing includes the use of feature selection methods to reduce the dimensionality of feature space.

As shown at block 314, the SVM is trained using the pre-processed data from the training data subset. Accordingly, the SVM is trained by adjusting its operating parameters until a desirable training output is achieved. The determination of whether a training output is desirable may be accomplished by comparing the training output to the known characteristics of the training data. A learning machine is considered to be trained when its training output is within a predetermined error threshold from the known characteristics of the training data.

As is known in the art, different kernels will cause a SVM to produce varying degrees of quality in the output for a given set of input data. Therefore, the selection of an appropriate kernel may be essential to the desired quality of the output of the SVM. In one embodiment of the learning machine, a kernel may be chosen based on prior performance knowledge, such as the relation of various clinical and laboratory variables to liver function relevant to bilirubin metabolism, transport, and excretion. As is known in the art, exemplary kernels include polynomial kernels, radial basis function (RBF) classifier kernels, linear kernels, etc. In an alternate embodiment, a customized kernel may be created that is specific to a particular problem or type of data set. The quality of the outputs for each simultaneously trained and tested SVM may be compared using a variety of selectable or weighted metrics to determine whether the kernel chosen performs sufficiently well or whether an alternative kernel achieves superior performance.

At block 318, the resulting classification table is examined by available receiver-operating characteristic (ROC) statistical software, to assess whether the classifier generated by the SVM meets the design requirements established for the predictive model. In the case of an embodiment of the present invention, a minimum ROC area-under-the-curve (C-statistic) of 0.80 is required before a model is an acceptable candidate for consideration for logistic regression and subsequent processing and validation. In the event that ROC is lower than the acceptable minimum, then additional iterations of variables selection, pre-processing, kernel generation, and SVM support vector generation are performed (steps 310-318). Alternatively, if ROC is determined to be acceptable at block 318, then the kernel and support vector are accepted and the model is validation-tested, as shown at block 320, using the test data subset that was previously prepared and reserved at block 308.

Based on the post-processed test output, it is determined at steps 322, 324, and 326 whether an optimal minimum was achieved by the SVM and logistic regression. Those skilled in the art should appreciate that a SVM is able to ascertain an output having a global minimum error. However, as mentioned above, output results of a SVM for a given data set will typically vary with kernel selection. Therefore, there are in fact multiple global minimums that may be ascertained by a SVM for a given set of data. As used herein, the term "optimal minimum" or "optimal solution" refers to a selected global minimum that is considered to be optimal (e.g. the optimal solution for a given set of problem specific, pre-established criteria) when compared to other global minimums ascertained by a SVM. Accordingly, at block 322, determining whether the optimal minimum has been ascertained may involve comparing the output of a SVM with a historical or predetermined value. In some embodiments of the present invention, the historical benchmark of classification is the receiver operating characteristic (ROC) for Bhutani's bilirubin nomogram.

If it is determined that the optimal minimum has not been achieved by the trained SVM, the method moves to block 310, and kernel selection is readjusted. Adjustment of the kernel selection may comprise selecting one or more new kernels or adjusting kernel parameters. Furthermore, in the case where multiple SVMs were trained and tested simultaneously, selected kernels may be replaced or modified while other kernels may be re-used for control purposes. After the kernel selection is adjusted, the method is repeated from block 312, where the pre-processed training data is input into the SVM for training purposes. When it is determined at block 322 that the optimal minimum has been achieved, test data is collected similarly as described above. By definition, live data has not been previously evaluated, so that the desired output characteristics that were known with respect to the training data and the test data are not known.

Additional test data is optionally collected in preparation for testing the trained SVM. Test data may be collected from one or more local and/or remote sources. In some embodiments, test data and training data may be collected from the same source(s) at the same time. Thus, test data and training data sets can be divided out of a common data set and stored in a local storage medium for use as different input data sets for a learning machine. Regardless of how the test data is collected, any test data used is pre-processed at block 310 in the same manner as was the training data. As should be apparent to those skilled in the art, a proper test of the learning may only be accomplished by using testing data of the same format as the training data. Then, at block 320, the learning machine is tested using the pre-processed test data, if any. The test output of the learning machine is optionally post-processed in order to determine if the results are desirable. Again, the post processing step involves interpreting the test output into a meaningful form. The meaningful form may be one that is readily understood by a human or one that is compatible with another processor. Regardless, the test output requires post-processing into a form which may be compared to the test data to determine whether the results were desirable. Examples of post-processing steps include but are not limited of the following: optimal categorization determinations, scaling techniques (linear and non-linear), transformations (linear and non-linear), and probability estimations (such as logit or probit equations).

After validation testing has confirmed a vector of variables and transformations that achieves acceptable sensitivity, specificity, and ROC performance, a logistic regression model is calculated, at block 324, utilizing the input variables and transformations that were developed and validated in the previous steps. The generation of the logistic regression model may be done using the training data subset or the entire original dataset or other partitions derived from it, depending on missing data for some variables or other pragmatic factors. Embodiments of the present invention do not depend upon any particular partitioning at this step. Indeed, the sample size available may often dictate what is possible to do, insofar as logistic regression does not tolerate missing data elements. If a decision is made to retain cases that contain missing data in the logistic regression step, then hot-deck or last-value-carry-forward, or other imputation methods may be used, such as are familiar to statisticians.

Finally, the statistical performance of the resulting logistic regression classifier, including its ROC c-statistic, is assessed and, if adequate to the intended purpose, accepted for implementation, as shown at blocks 326 and 328.

Figure 4:
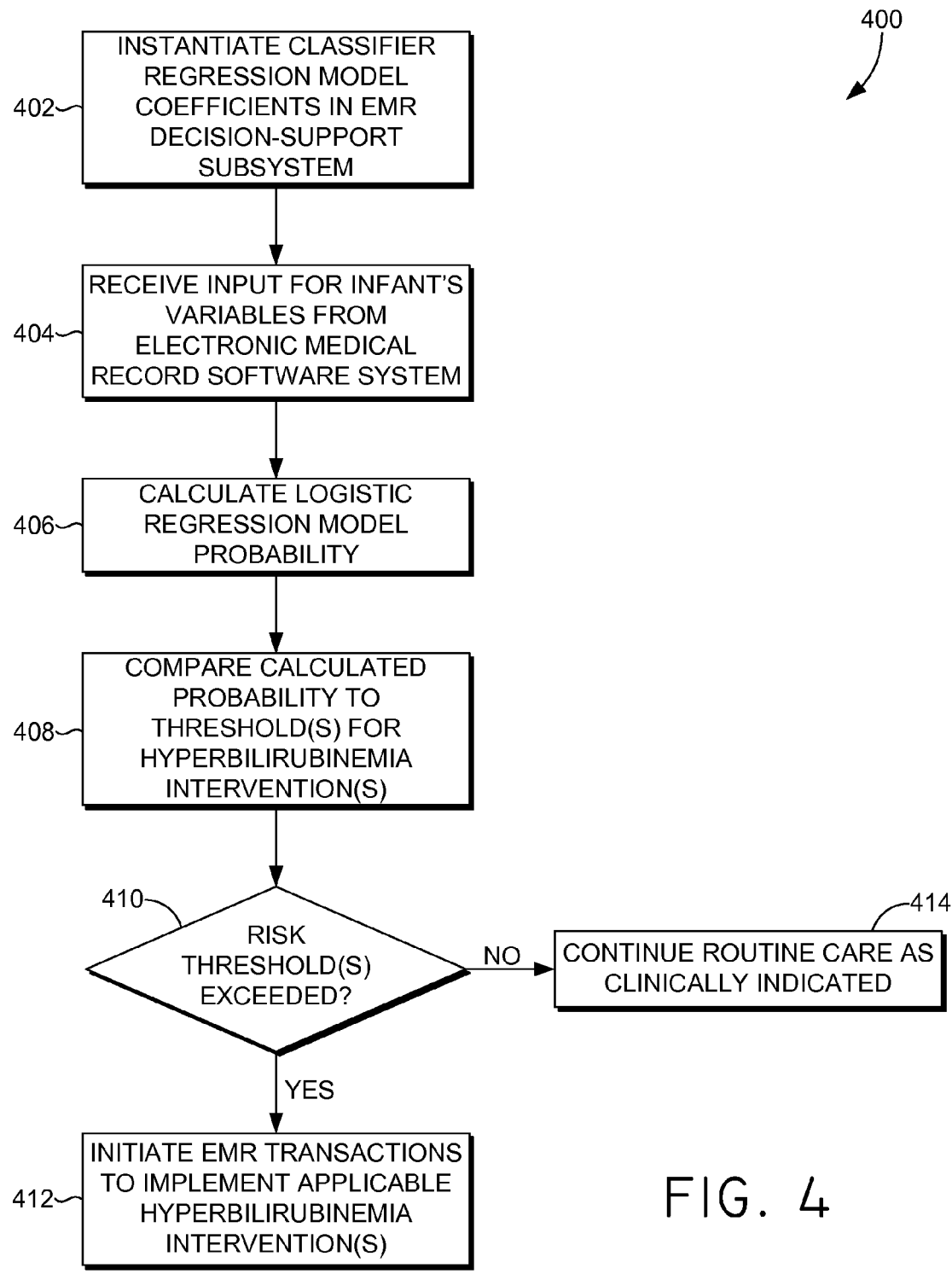
FIG. 4 is a flow diagram showing a method for prospectively classifying an infant's probability of neonatal hyperbilirubinemia employing a statistical model in accordance with an embodiment of the present invention.

Turning now to FIG. 4, a flow diagram is provided that illustrates an exemplary optimal categorization method 400 that may be used for pre-processing data or post-processing output from a learning machine in accordance with an embodiment of the present invention. Additionally, as will be described in further detail below, the exemplary optimal categorization method 400 may be used as a stand-alone categorization technique, independent from learning machines. The exemplary optimal categorization method 400 begins in block 402, where classifier regression model coefficients in a medical/health record (e.g., EMR) decision-support subsystem are instantiated. At block 404, an input data set for a particular infant is received.

In one embodiment, the statistical model is embedded within an electronic medical record software system capable of receiving or retrieving the required variables' values and producing a calculated risk score for presentation to the physician or other qualified decision-makers. In another embodiment, the statistical model is deployed in standalone software, either on an internet web portal, for instance in JAVA or ASP application software, or in a portable device such as a PDA or cellphone. In these embodiments, the user provides the input data for the risk score to be calculated.

The decision-support subsystem receives input information for each of the classifier variables. When the variables' values have been entered, either by retrieving the information from the EMR or by manual entry by the clinician user, for instance, the probability of hyperbilirubinemic re-admission is determined using the logistic regression equations that were generated and validated using a method such as the method 300 described hereinabove, as shown at block 406. The classifier's predicted probability is compared, as shown at block 408, to thresholds that the clinician user's institution or pediatrics professional societies or other policy makers have set to govern the decision about giving or withholding certain interventions that aim to prevent hyperbilirubinemia readmissions, such as holding the newborn for a longer time in the hospital or discharging the newborn with photo-therapy equipment. If one or more of the applicable policy-related risk thresholds are determined to be exceeded, at block 410, then the user is directed, at block 412, to initiate appropriate implementation of indicated interventions. If the thresholds are not transgressed, then at block 414, the user is directed to implement routine care and discharge-planning for the infant.

As mentioned above, the exemplary optimal categorization method 400 may be used in pre-processing data and/or post-processing the output of a learning machine. For example, as a preprocessing transformation step, the exemplary optimal categorization method 400 may be used to extract classification information from raw data. As a post-processing technique, the exemplary optimal categorization method 400 may be used to determine the optimal cut-off values for markers objectively based on data, rather than relying on ad hoc approaches. As should be apparent, the exemplary optimal categorization method 400 has applications in pattern recognition, classification, regression problems, etc. The exemplary optimal categorization method 400 may also be used as a stand-alone categorization technique, independent from SVMs and other machine learning algorithms.

An embodiment of the present invention will now be described with reference to FIG. 5, which illustrates an exemplary screen display 500 providing information regarding the probability of hyperbilirubinemia for a newborn using a logistic model. It will be understood and appreciated by those of ordinary skill in the art that the screen display of FIG. 5 is provided by way of example only and is not intended to limit the scope of the present invention in any way.

Figure 5:
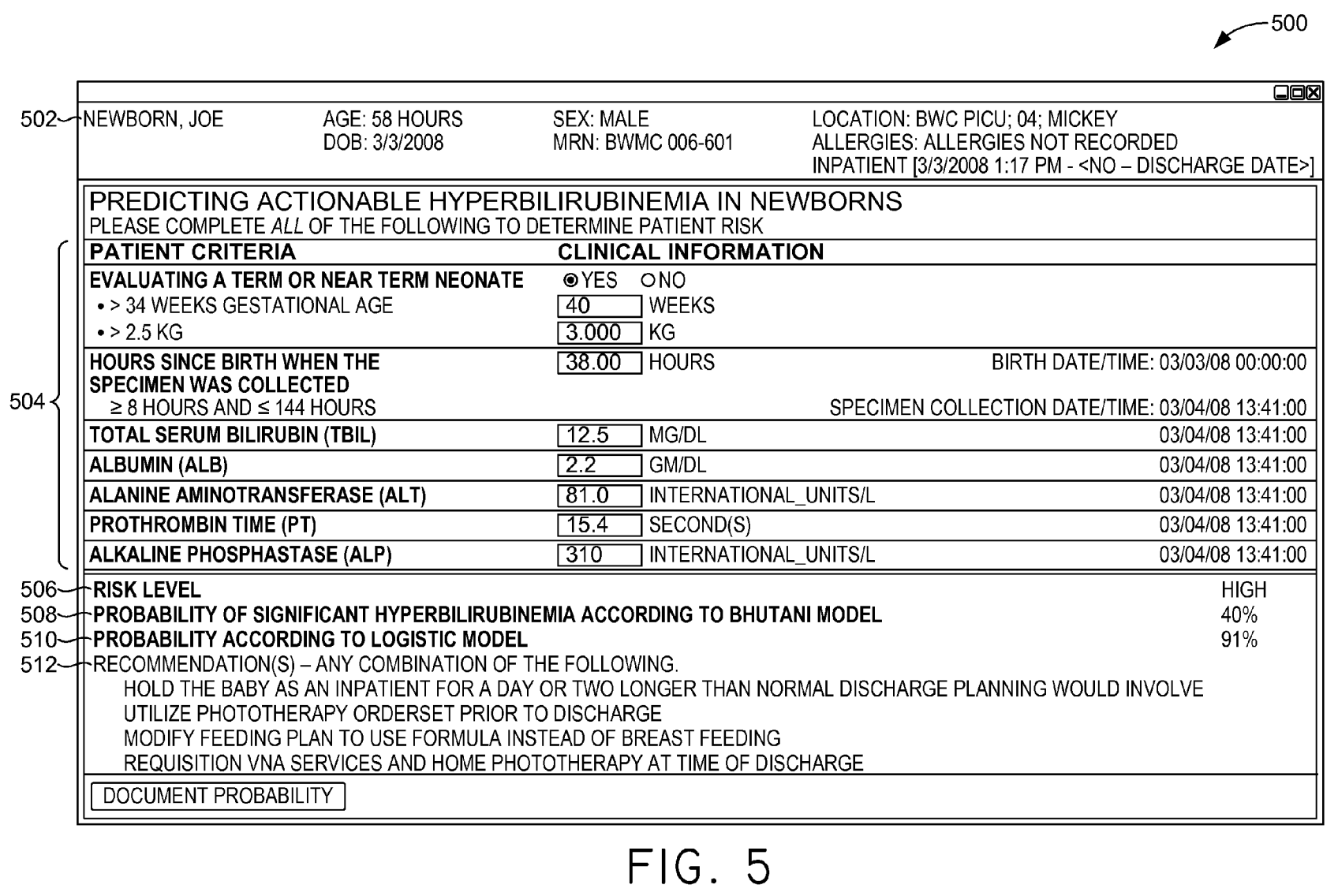

As shown in FIG. 5, the screen display 500 includes a patient information area 502 providing general information regarding the newborn currently being evaluated, including the newborn's name, age, date of birth, sex, and other general patient information. The screen display also includes a patient criteria area 504. The patient criteria area 504 allows a clinician to enter the input data set that is used in conjunction with a logistic regression model developed, for instance, using the method 300 described above with reference to FIGS. 3A and 3B to generate a probability of hyperbilirubinemia for the newborn. In the present example, the patient criteria area 504 includes the following variables: whether the newborn is a term or near term neonate, gestational age, birth weight, time after birth specimen was collected, total serum bilirubin, albumin, alanine, aminotransferase, prothrombin, and alkaline phosphatase. Although FIG. 5 illustrates a screen display in which a clinician enters data values for the displayed variables in the patient criteria area 504, in embodiments of the present invention, all or a portion of the values may be populated automatically by the system retrieving the values from an electronic medical record for the newborn.

The screen display 500 also displays information regarding the probability of hyperbilirubinemia determined based on the input data from the patient criteria area 504 and the logistic regression model. In particular, the screen display 500 provides a probability of hyperbilirubinemia using the logistic regression model 510. Additionally, the screen display 500 provides a risk level 506 associated with the probability of hyperbilirubinemia calculated using the logistic regression model. As a comparison value, the probability of hyperbilirubinemia using the Bhutani model 508 is also presented. In the present example, the probability of hyperbilirubinemia using the logistic regression model 510 is 91% while the probability of hyperbilirubinemia using the Bhutani model is only 40%. As such, the present example illustrates a newborn case in which using the Bhutani model alone would not have recognized the hyperbilirunemia risk for the newborn. In contrast, the logistic regression model was able to recognize the higher probability of hyperbilirubinemia and indicates a "High" risk level 506. Based on the determination of a "High" risk level 506, the screen display 500 presents a number of recommended interventions 512. The clinician may review the probability information and recommended interventions 512 and determine the appropriate course of treatment for the infant.

Exemplary System Implementation

The population of neonates in a collection of birth centers was screened, according to an embodiment of the invention, to determine the subpopulation with a high probability of becoming affected by jaundice caused by excess bilirubin production and/or deficient bilirubin metabolism and excretion. The screen included a non-invasive test, which was administered within a few hours after birth, preferably less than 48 hours after birth.

Deidentified HIPAA-compliant Electronic Medical Record (EMR) data were retrieved for a total of 48,575 neonates in Cerner Corporation's Health Facts™ data warehouse who were born and discharged from U.S. hospitals between Jan. 1, 2000 and Sep. 30, 2007. Clinical, laboratory, and pharmacy data elements were available for each of the neonates. Retrospective, exploratory statistical analysis was performed using the open-source support vector machine (SVM) software, mySVM. Only those variables having missing-data rates less than 20% were retained in the kernel and support vector and subsequent multi-variable logistic regression model. Sub-analysis was performed on 423 neonate re-admissions for whom post-delivery serial bilirubin and other pre-discharge laboratory data plus clinical and laboratory data at the time of re-presentation was performed using the Health Facts™ neonatal data.

The above modeling methods provide broad approaches of combining clinical laboratory tests and, optionally, the expression of genes to predict subsequent hyperbilirubinemia that is sufficiently severe to be associated with readmission of the infant to hospital. One could also provide no weight in a simple voting method or determine weights in a supervised or unsupervised method using agglomerate, divisive, or random approaches. All or selected combinations of variables may be combined in ordered, agglomerate, or divisive, supervised or unsupervised clustering algorithms with unknown samples for classification. Any form of correlation matrix may also be used to classify unknown samples. The spread of the group distribution and discriminate score alone provide enough information to enable a skilled person to generate all of the above types of models with accuracy that can exceed discriminate ability of individual laboratory tests (biomarkers or genes). Some examples of methods that could be used individually or in combination after transformation of data types include but are not limited to: Discriminant Analysis, Multiple Discriminant Analysis, logistic regression, multiple regression analysis, linear regression analysis, conjoint analysis, canonical correlation, hierarchical cluster analysis, k-means cluster analysis, self-organizing maps, multidimensional scaling, structural equation modeling, support vector machine determined boundaries, factor analysis, neural networks, bayesian classifications, and resampling methods.

Learning machines, such as support vector machines (SVMs), can be used to analyze datasets to recognize patterns within the dataset using kernels that are selected according to the nature of the data to be analyzed. Where the datasets possesses structural characteristics, locational kernels can be utilized to provide measures of similarity among cases within the dataset. The locational kernels are then combined to generate a decision function, or kernel, that can be used to analyze the dataset. Where invariance transformations or noise is present, tangent vectors are defined to identify relationships between the invariance or noise and the data points. A covariance matrix is formed using the tangent vectors, then used in generation of the kernel for recognizing patterns in the dataset.

In recent years, machine-learning approaches for data analysis have been widely explored for recognizing patterns which, in turn, allow extraction of significant information contained within a large data set that may also include data consisting of nothing more than irrelevant detail. Learning machines comprise algorithms that may be trained to generalize using data with known outcomes. Trained learning machine algorithms may then be applied to predict the outcome in cases of unknown outcome, i.e., to classify the data according to learned patterns. Machine-learning approaches, which include neural networks, hidden Markov models, belief networks and kernel-based classifiers such as SVMx, are ideally suited for domains characterized by the existence of large amounts of data, noisy patterns and the absence of general theories. Support vector machines (SVMs) are disclosed, for instance, in U.S. Pat. Nos. 6,128,608 and 6,157,921. However, embodiments of the present invention do not require use of an SVM; any of a variety of other conventional statistical methods known to those practiced in the art could have been utilized. Likewise, through the exemplary implementation, use of an SVM was not required for its practice.

Many successful approaches to pattern classification, regression, clustering, and novelty detection problems rely on kernels for determining the similarity of a pair of patterns. These kernels are usually defined for patterns that can be represented as a vector of real numbers. For example, the liner kernels, radial basis function kernels, and polynomial kernels all measure the similarity of a pair of real vectors. Such kernels are appropriate when the patterns are best represented in this way, as a sequence of real numbers. The choice of a kernel corresponds to the choice of representation of the data in a feature space. In many applications, the patterns have a greater degree of structure. This structure can be exploited to improve the performance of the learning system. Examples of the types of structured data that commonly occur in machine learning applications are strings, such as DNA sequences, and documents; trees, such as parse trees used in natural language processing; graphs, such as web sites or chemical molecules; signals, such as ECG signals and microarray expression profiles; spectra; images; spatio-temporal data; and relational data, among others.

For high-dimensionality classification problems, SVM kernel methods generally involve first finding a mapping from the available measured variables to a vector of real numbers. In the exemplary implementation, the laboratory biomarkers that were retained in the SVM and in the subsequent logistic regression model are ones that are known to be associated with liver developmental maturity and with cellular metabolic and excretory functions of the liver:

Total bilirubin in mg/dL (serum TBIL);
Alanine aminotransferase in U/L (serum ALT);
Alkaline phosphatase in U/L (serum ALKP);
Albumin in gm/dL (serum ALB);
Prothrombin time in sec (Protime or INR);
Gestational age in weeks;
Birth weight in grams; and
Specimen collection time, in hours since birth (known with precision not less than ±1 hr).

The ROC c-statistic performance of the Bhutani nomogram has been reported to be 78%. Therefore, any system and method that aims to deliver predictive accuracy and calibration should exceed this figure to be useful.

Validation testing of the statistical model of embodiments of the present invention was performed using a randomly selected subset of 23,897 neonates from HealthFacts™. The statistical sensitivity of the model in this cohort was 92% and the specificity was 89% for predicting re-admissions to hospital within 10 days after routine newborn discharge. The ROC c-statistic was 97%, significantly improving upon the Bhutani and Keren nomograms' accuracy.

Additional prospective validation testing was performed using a cohort of 3,411 neonates whose EMR data were extracted from the HealthFacts™ data warehouse for the same U.S. institutions whose cases had contributed to the training and test data subsets for the design, development, and validation testing of the invention. This prospective cohort comprised neonates born and discharged from these institutions over a 12 month period. The statistical sensitivity of the model in this cohort was 93% and the specificity was 94% for predicting re-admissions to hospital within 10 days after routine newborn discharge. The ROC c-statistic was 96%.

As can be understood, embodiments of the present invention provide for identifying newborns at risk of clinically significant hyperbilirubinemia using a multiple variable predictive score and administering interventions to at-risk newborns. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. One or more computer storage media storing computer-useable instructions that, when used by one or more computing devices, cause the one or more computing devices to perform a method comprising:
  (a) receiving training data associated with a plurality of human infant cases, the plurality of human infant cases having been selected based on inclusion-exclusion criteria, the training data including data for a plurality of variables;
  (b) partitioning the training data into a training data subset and a test data subset, each of the training data subset and the test data subset including training data associated with a portion of the plurality of human infant cases;
  (c) employing a machine-learning technique to generate a classifier based on the training data subset;
  (d) assessing whether the classifier satisfies a predetermined receiver operating characteristic (ROC) c-statistic;
  (e) if the classifier does not satisfy the predetermined ROC c-statistic, repeating (c) and (d) until a classifier is generated that satisfies the predetermined ROC;
  (f) if the classifier satisfies the predetermined ROC c-statistic, validation testing the classifier using the test data subset;
  (g) assessing whether an optimum minimum has been achieved based on output from the validation testing;
  (h) if an optimum minimum has not been achieved, repeating (c)-(g) until an optimum minimum has been achieved;
  (i) if an optimum minimum has been achieved, generating a multi-variable logistic regression model capable of calculating a probability of clinically significant hyperbilirubinemia using the plurality of variables;
  (j) assessing whether statistical performance of the multi-variable logistic regression model satisfies a predetermined requirement;
  (k) if the statistical performance of the multi-variable logistic regression model does not satisfy the predetermined requirement, repeating (c)-(j) until a multi-variable logistic regression model is generated that satisfies the predetermine requirement;
  (l) receiving input data for a human infant, the input data including laboratory test results for the human infant determined from measurements received at a single measurement-session time and including a time from birth associated with the laboratory test results;
  (m) calculating a probability of clinically significant hyperbilirubinemia using the input data for the human infant and the multi-variable logistic regression model;
  (n) comparing the calculated probability to one or more thresholds for hyperbilirubinemia intervention to determine one or more risk levels; and
  (o) communicating for presentation to a clinician the one or more risk levels.

2. The one or more computer storage media of claim 1, wherein the training data is received from one or more selected from the following: a research facility, an academic institution, a commercial entity, a public source, and a private source.

3. The one or more computer storage media of claim 1, wherein the plurality of variables are predetermined based on analysis of medical records for human infants to identify available variables.

4. The one or more computer storage media of claim 1, wherein the plurality of variables includes one or more selected from the following: total bilirubin; alanine aminotransferase; alkaline phosphatase; albumin; prothrombin time; gestation age; and birth weight.

5. The one or more computer storage media of claim 1, wherein the inclusion-exclusion criteria is based on one or more selected from the following: gestational age at birth; birth weight; meconium-stained amniotic fluid; early onset neonatal sepsis; congenital malfunction; parental HIPAA informed consent declination; bilirubin determination prior to newborn discharge from hospital; and bilirubin-associated care episode within the first 30 days following newborn discharge from hospital.

6. The one or more computer storage media of claim 1, wherein the method further comprises pre-processing training data.

7. The one or more computer storage media of claim 1, wherein the machine-learning technique employs a support vector machine.

8. The one or more computer storage media of claim 1, wherein the input data for the human infant is automatically retrieved from an electronic medical record.

9. The one or more computer storage media of claim 1, wherein the method further comprises communicating for presentation to the clinician one or more indicated interventions associated with the one or more risk levels.

* * * * *